United States Patent [19]

Pospisil

[11] Patent Number: 4,464,940

[45] Date of Patent: Aug. 14, 1984

[54] SAMPLER FOR A GAS CHROMATOGRAPH

[75] Inventor: Peter Pospisil, Uberlingen, Fed. Rep. of Germany

[73] Assignee: Bodenseewerk Perkin-Elmer & Co., GmbH, Uberlingen, Fed. Rep. of Germany

[21] Appl. No.: 397,305

[22] Filed: Jul. 12, 1982

[30] Foreign Application Priority Data

Jul. 29, 1981 [DE] Fed. Rep. of Germany ....... 3129833

[51] Int. Cl.$^3$ .............................................. G01N 1/14
[52] U.S. Cl. ............................ 73/864.21; 73/864.23; 73/864.81
[58] Field of Search ........... 73/864.21, 864.22, 864.23, 73/864.24, 864.25, 864.74, 864.81

[56] References Cited

U.S. PATENT DOCUMENTS 3,668,834  6/1972  Deans .............................. 73/864.81
4,237,733 12/1980  Kolb et al. ...................... 73/864.23

*Primary Examiner*—S. Clement Swisher
*Attorney, Agent, or Firm*—F. L. Masselle; E. T. Grimes; R. A. Hays

[57] ABSTRACT

According to the head space method, samples are supplied from sealed sample vessels by means of a needle. A change-over valve, an optionally higher or reduced carrier gas pressure is applied to a carrier gas conduit comprising a shut-off valve and terminating between the needle and entrance of the separating column. This enables a defined sample feeding and analysis by an optimum carrier gas pressure even with volatile samples.

2 Claims, 3 Drawing Figures

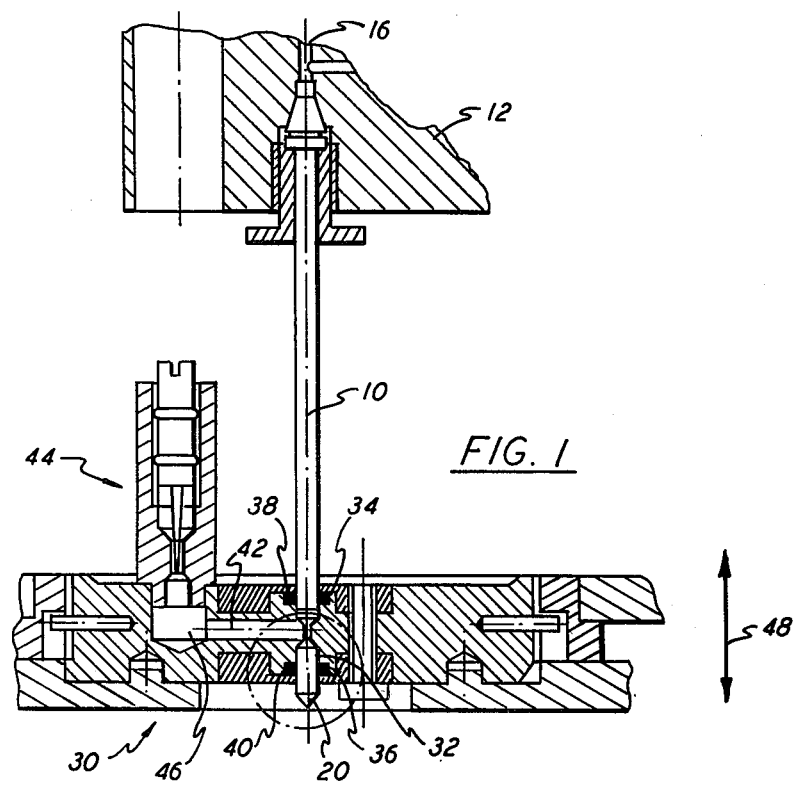
FIG. 1
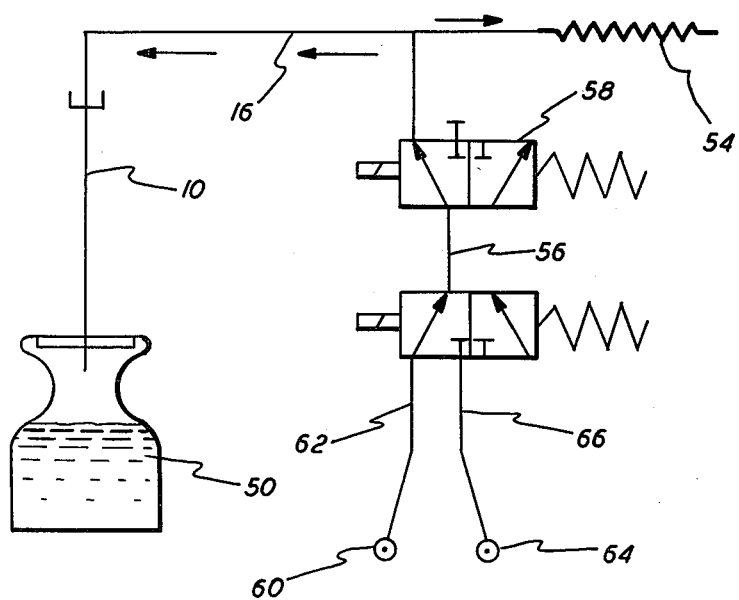
FIG. 2
FIG. 3

SAMPLER FOR A GAS CHROMATOGRAPH

BACKGROUND OF THE INVENTION

The present invention generally relates to a head space sampler for use with a gas chromatograph and, in particular, relates to a sampler having means for selectively providing either a comparatively higher or a comparatively lower carrier gas pressure.

In a sealed sample vessel, a state of equilibrium exists in the head space above a liquid sample. In the head space the partial pressures of the individual sample components are proportional to their concentrations in the liquid sample. In a sampler operating according to the head space method, a metered volume of sample from the head space of the sample vessel is delivered to the inlet of a gas chromatograph. The composition of the liquid sample in the sample vessel is then determined from the composition of the head space sample.

In one conventional sampler (German Pat. No. 1 284 660), the sample vessels are sealed by a self-sealing diaphragm or septum. A needle is pierced through this self-sealing diaphragm, which needle is connected to the entrance of the separating column of a gas chromatograph. The entrance of the separating column is in turn connected to a carrier gas conduit arranged to be closed by a solenoid valve. When the solenoid valve is opened, the carrier gas pressure at the entrance of the separating column is transferred to the head space of the sample vessel through the needle acting as a capillary whereby an increased pressure is built up therein. The partial pressures of the sample components, however, are not affected. After closing the carrier gas conduit, for example, by means of the solenoid valve, the pressure at the entrance of the separating column breaks down. Now carrier gas plus sample vapor flows from the head space to the inlet portion of the gas chromatograph at the entrance of the separating column. The volume sampled in this fashion is determined by the time interval during which the solenoid valve in the carrier gas conduit is closed.

Ordinarily, to achieve reproducible results and sufficient vapor pressures, the sample vessels are normally thermostated at an elevated temperature (German Offenlegungsschrift No. 2 818 251).

A particular pressure exists for the optimum separation of the sample in the separating column, which pressure should be applied to the entrance of the separating column during the analysis. If there are highly volatile samples to be applied, it may occur that, during the pre-heating in the closed sample vessels, a pressure exceeding the optimum pressure mentioned is created. This occurs most frequently in capillary columns having very small flow resistance requiring very low inlet-pressure for producing the optimum flow.

If such a pressure is chosen after the piercing of the needle into the head space, no carrier gas flows into the sample vessel for building up the pressure, but from the beginning vapor flows out of the head space against the lower carrier gas pressure to the separating column. The flow from the head space to the column is not interrupted thereby, even if the solenoid valve transitorily closed in the carrier gas conduit, is re-opened after the dosing. Therefore, a defined sampling is not possible.

SUMMARY OF THE INVENTION

Accordingly, it is one object of the present invention to provide a sampler adapted to exactly define a sample volume and which operates at an optimum carrier gas pressure even with samples which build up a relatively high pressure in the head space.

This object is achieved, at least in part, by a sampler having a means for generating a first higher carrier gas pressure at a first carrier gas connection, a means for generating a second carrier gas pressure, which is reduced compared to the first one, at a second carrier gas connection, and including a change-over valve by means of which either the first or the second carrier gas connection can be connected to the carrier gas conduit.

Hence, by employing a higher pressure, a guilding up of pressure in the sample vessel is effected, or at least a premature overflowing of sample vapors can be prevented. Further, when the closure valve is subsequently closed and the sampling is carried out in the usual manner, a defined volume of sample vapor is transferred to the entrance of the separating column. The sampling is interrupted by re-applying the first higher carrier gas pressure. After the needle is removed from the sample vessel, change-over to the second reduced carrier gas pressure takes place. This occurs when the exit of the needle is preferably connected to atmosphere through a restrictor, and this carrier gas pressure may be selected such that the optimum flow results therefrom.

Other objects and advantages will become apparent to those skilled in the art from the following detailed specification in conjunction with the accompanying drawing.

BRIEF DESCRIPTION OF THE DRAWING

An embodiment of the present invention is described in greater detail hereinafter with reference to the accompaying drawing, in which:

FIG. 1 shows a sectional view of a needle assembly;
FIG. 2 shows an enlarged detail "X" of FIG. 1;
FIG. 3 is a schematic of a pneumatic circuit of the needle, the separating column and the shut-off and change-over valves.

DETAILED DESCRIPTION OF THE INVENTION

In FIG. 1, a needle, generally designated at 10, is fixed in the injection block 12 of a gas chromatograph. The needle 10 has a longitudinal passage 14 connected to a connecting passage 16 in the injection block 12. The longitudinal passage 14 is connected to a transverse bore of the needle 10. The transverse bore forms a lateral exit aperture 18. A tip 20 is located at the end of the needle. The tip 20 is provided at an end piece 22 pressed into an enlargement of the longitudinal bore 14 and closing longitudinal bore 14 at its end face. Thus, carrier gas flows from the connecting passage 16 through the longitudinal bore 14 and laterally out of the exit aperture 18.

Preferably, the needle 10 has a somewhat thicker wall thickness than conventional needles. For example, needle 10 preferably has an outer diameter of 1.5 mm, whereas, in conventional apparatus, needles usually have an outer diameter of about 1 mm. In addition, needle 10 provides a circumferential groove 24 in the area of exit aperture 18. The lateral exit aperture 18 terminates on the bottom of the circumferential groove 24. The lateral walls 26 and 28 of the circumferential groove 24 are preferably tapered such that the circumferential groove 24 becomes wider to the outside. Preferably, the edges of the circumferential groove 24 are rounded and polished.

A housing 30 includes a housing bore 32. The housing bore 32 is surrounded by two spaced apart annular grooves, 34 and 36, in which sealing rings 38 and 40, respectively, preferably in the form of O-rings, are mounted. A lateral outlet passage 42 branches off the housing bore 32 between the sealing rings 38 and 40. The outlet passage 42 is connected to the atmosphere through a restrictor 44. To this end, outlet passage 42 ends in a blind bore 46 extending substantially parallel to the housing bore 32. The adjustable restrictor 44, designed, in this embodiment, as a needle valve, is disposed in the blind bore 46.

The needle 10 extends through the housing bore 32. The sealing rings 38 sealingly engage the outer surface of the needle 10 and create a gaseous seal between the needle 10 and the housing bore 32. The housing 30 is guided to be moved in parallel to the needle 10, as indicated by the double arrow 48. In the position of rest, illustrated in FIG. 1, the outlet aperture 18 is located between the sealing rings 38 and 40. It is connected to the outlet passage 42 via the circumferential groove 24.

If a sample vessel 50, see FIG. 3, which is sealed by a self-sealing diaphragm, i.e. a septum, is urged against the housing 30 from below, the housing 30 is pushed upward relative to the stationary needle 10. In this fashion, needle 10 pierces through the diaphragm of the sample vessel by means of its tip 20. Sealing ring 36 passes by the exit aperture 18 of needle 10. The exit aperture 18 enters the head space of the sample vessel through the diaphragm. The connecting passage 16 is now, to a large extent, unrestrictedly connected to the head space of the sample vessel by means of the longitudinal passage 14 and the exit aperture 18.

A preferred constructive design of a needle assembly is the subject matter of U.S. patent application Ser. No. 354,409, filed Mar. 3, 1982, corresponding to West German patent application No. P 31 09 616.6, not prepublished which is assigned to the assignee hereof. The above-identified patent application is deemed to be incorporated by reference herein.

The connecting passage 16 connects needle 10 to the entrance 52 of a gas chromatographic separating column 54. A carrier gas conduit 56 ends in the connecting passage 16 between needle 10 and separating column 54. A controllable closure valve 58, for example as a solenoid valve, is disposed in the carrier gas conduit 56. Means 60 are provided for generating a first relatively high carrier gas pressure at a first carrier gas connection 62. Further, means 64 are provided for generating a comparatively lower second carrier gas pressure. Alternatively, the first and the second carrier gas connections, 62 or 66, respectively, may be connected to the carrier gas conduit by means of a change-over valve 68, also designed herein as a solenoid valve.

In the condition illustrated in FIG. 3, increased pressure from the carrier gas connection 62 is effective at the entrance 52 of the separating column 54. This increased pressure is transferred to the head space of the sample vessel 50 via the connecting conduit 16 and the needle 10. The pressure generated at the carrier gas connection 62 by the means 60 is sufficiently high that, even with volatile samples, no flow from the sample vessel 50 against the carrier gas pressure into the connecting passage 16 takes place. Sample feeding is caused by closing valve 58 whereupon the pressure at the entrance 52 of the separating column breaks down such that sample vapor flows from the head space of the sample vessel 50 through the needle 10 and the connecting passage 16 to the separating column 54. To terminate the sample vapor flow, valve 58 is reopened. The needle 10 is removed from the sample vessel 50 and reaches the position illustraed in FIG. 1. Simultaneously, the change-over valve 68 is switched and applies, from the means 64 through carrier gas connection 66, the reduced second carrier gas pressure optimum for the operation of the separating column 54, to the entrance of the separating column 54. By means of this pressure, the sample supplied is transported through the separating column 54. A flushing flow flows through needle 10 as well as outlet passage 42 and restrictor 44, which flushing flow cleans the assembly from remnants of the sample vapor just supplied.

Although the present assembly has been described herein by way of a specific example, other configurations and arrangements can also be used without departing from the spirit and scope of the present invention. The above detailed description is exemplary and is not deemed limiting. Hence, the scope of the present invention is considered defined by the appended claims and the reasonable interpretation thereof.

What is claimed is:

1. A head space sampler for a gas chromatograph, said sampler comprising:
   a needle connected to the entrance of a gas chromatographic separating column by means of a connecting passage;
   a carrier gas conduit terminating at said connecting passage between said needle and said separating column;
   means for generating a first higher carrier gas pressure at a first carrier gas connection;
   means for generating a second carrier gas pressure, which pressure is comparatively lower that said said first pressure, at a second carrier gas connection;
   a change-over valve, said change-over valve having said first and second carrier gas connection as inputs and said carrier gas conduit as an output;
   a controllable shut-off valve disposed in said carrier gas conduit between said change-over valve and said termination of said carrier gas conduit at said connecting passage; and
   means for piercing said needle through a septum of a sample vessel into the head space thereof.

2. Sampler as claimed in claim 1 wherein said change-over valve and said controllable shut-off valve are solenoid valves.

* * * * *